US006454755B1

(12) United States Patent
Godshall

(10) Patent No.: US 6,454,755 B1
(45) Date of Patent: Sep. 24, 2002

(54) METHOD AND APPARATUS FOR TRANSDERMAL DELIVERY OF COMPOUNDS UTILIZING DISRUPTION OF THE EPIDERMIS

(75) Inventor: Ned Allen Godshall, Albuquerque, NM (US)

(73) Assignee: Silicon MicroDevices, Albuquerque, NM (US)

( * ) Notice: Subject to any disclaimer, the term of this patent is extended or adjusted under 35 U.S.C. 154(b) by 697 days.

(21) Appl. No.: 08/845,503

(22) Filed: Apr. 24, 1997

Related U.S. Application Data

(63) Continuation-in-part of application No. 08/445,695, filed on May 22, 1995.

(51) Int. Cl.[7] .................................................. A61N 1/30
(52) U.S. Cl. .......................... 604/501; 604/20; 424/449
(58) Field of Search ............................. 604/20–21, 501; 424/449

(56) References Cited

U.S. PATENT DOCUMENTS 3,814,097 A * 6/1974 Ganderton et al.
3,964,482 A * 6/1976 Gerstel et al.
5,279,543 A * 1/1994 Glikfeld et al.
5,279,544 A * 1/1994 Gross et al.
5,983,136 A * 11/1999 Kamen
6,219,574 B1 * 4/2001 Cormier et al.
6,230,051 B1 * 5/2001 Cormier et al.

FOREIGN PATENT DOCUMENTS

SU 1296174 * 3/1987

* cited by examiner

*Primary Examiner*—Mark Bockelman
(74) *Attorney, Agent, or Firm*—Gray, Cary, Ware & Freidenrich

(57) ABSTRACT

A drug delivery system including an apparatus for mechanically disrupting a layer of skin having a known thickness without substantially disrupting underlying dermis layers below the layer of skin in question and a reservoir for continuously applying the drug to the disrupted area of skin. The apparatus includes a cutter having a plurality of microprotrusions having a height chosen with respect to the layer of skin that is to be disrupted and a stop for preventing the apparatus from penetrating the skin beyond a predetermined distance. In the preferred embodiment of the present invention, the microprotrusions include blades that generate cuts in the layer of skin. The cuts are generated by moving the apparatus parallel to the surface of the skin either at the time of application, during the normal movements of the individual wearing the apparatus, or both. In the preferred embodiment of the present invention, the proper length of blade is determined for each individual and delivery site on that individual.

8 Claims, 3 Drawing Sheets

200
202 206 202 206 202
207 210 210 210
205 205 205 205 205 205
209 204

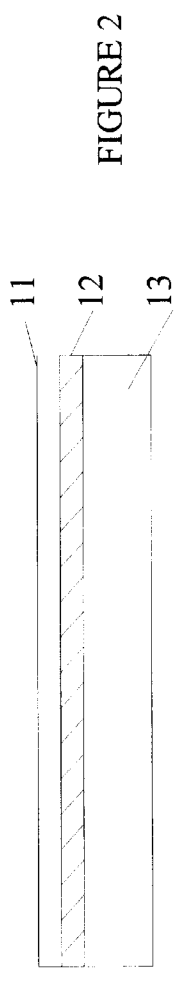
FIGURE 2
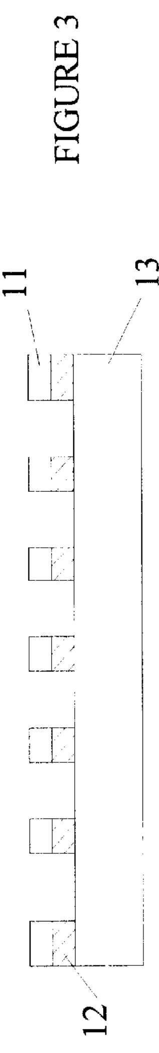
FIGURE 3
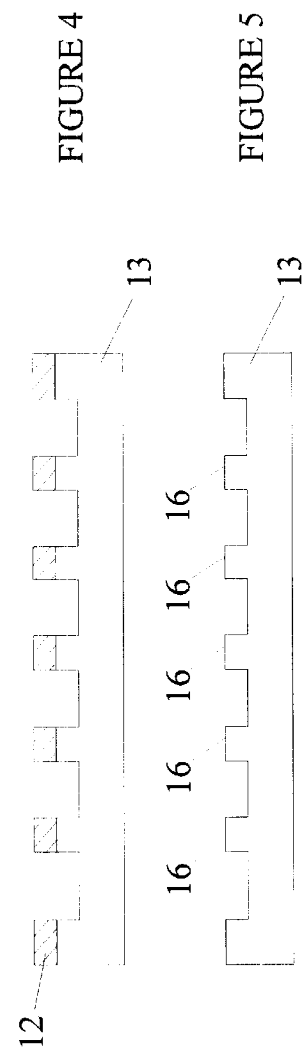
FIGURE 4
FIGURE 5
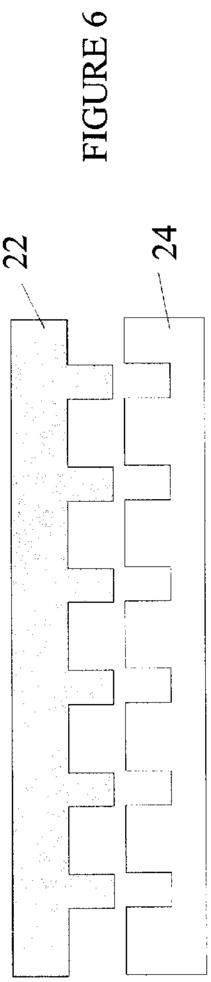
FIGURE 6

300
CHAMBER
302
310
STRATUM
CORNEUM
330
EPIDERMIS
331
DERMIS
333
350

METHOD AND APPARATUS FOR TRANSDERMAL DELIVERY OF COMPOUNDS UTILIZING DISRUPTION OF THE EPIDERMIS

RELATED APPLICATIONS

This application is a Continuation-in-Part of U.S. patent application Ser. No. 08/445,695 filed May 22, 1995.

FIELD OF THE INVENTION

The present invention relates to drug delivery systems, and more particularly, to a mechanical device that alters the outermost layer of skin for the improved delivery of compounds through the skin.

BACKGROUND OF THE INVENTION

Transdermal delivery of medication is well known in the prior art. Transdermal patches are available for a number of drugs. Commercially available examples of transdermal patches include scopolamine for the prevention of motion sickness, nicotine for aid in smoking cessation, nitroglycerin for the treatment of coronary angina pain, and estrogen for hormonal replacement. Generally, these systems have drug reservoirs sandwiched between an impervious backing and a membrane face which controls the steady state rate of drug delivery. The systems usually are attached to the skin by an adhesive gel with the membrane face adjacent to the skin.

Transdermal medication has significant advantages over both hypodermic injection and oral administration. A transdermal patch can provide significantly greater effective blood levels of a beneficial drug because the drug is not delivered in spike concentrations as is the case with hypodermic injection and most oral administration. In addition, drugs administered via transdermal patches are not subjected to the harsh environment of the digestive tract. Hence, in principle, transdermal delivery provides a method for administrating drugs that would otherwise need to be administered via hypodermic injection or intravenous infusion because the drug is destroyed in the digestive tract or immediately absorbed by the liver. Conversely, the digestive tract and liver are not subjected to the drug in transdermal administration. Many drugs, such as aspirin, have an adverse effect on the digestive tract.

Prior art transdermal drug delivery systems may be divided into passive diffusion and active transport systems. Transdermal drug delivery by diffusion is by far the most common of the transdermal methods. The nicotine patch is an example of this method of delivery (U.S. Pat. No. 4,597,961 to Frank T. Etscorn). This process is based on presenting the medication in a high dose external to the dermis and allowing the chemical to diffuse into and through the skin. The degree of diffusion depends on the porosity of the skin, the size and polarity of the drug molecules, and the concentration gradient across the stratum corneum, the outermost layer of human skin. These factors generally limit this mode of delivery to a very small number of useful drugs with very small molecules or unique electrical characteristics.

There have been two types of systems proposed to overcome the limited range of compounds that may be administered transdermally. The first class of techniques are based on the disruption of the skin to remove the diffusion barrier. One such method is described in U.S. Pat. No. 3,964,482. This technique utilizes an array of needle like protrusions that penetrate the stratum corneum. The drug is delivered either through the needles or on the surface of the skin. In the this case, the drug flows along the outer surface of the "needle" through the hole in the stratum corneum created by the needle. The length of the needles utilized in this invention is just long enough to penetrate the stratum corneum. Since the stratum corneum does not contain blood vessels or nerve endings, the patient does not experience bleeding or discomfort from the penetration of the needles.

While this device has been known for over 25 years, devices of this type have not been commercially successful. The disruption of the stratum corneum is not sufficient to render the skin sufficiently permeable to allow many compounds of interest to be administered transdermally.

Attempts to widen the range of drugs that may be transdermally delivered have also led to the active methods mentioned above. The active diffusion systems involve iontophoresis, electroporation, and ultrasound to increase the migration of the drug across the skin barrier. These methods attempt to electrically assist diffusion of the medication or apply high frequency electrical pulses or soundwaves to the skin to improve absorption. Unfortunately, the high cost and inconvenience of providing portable electrical equipment have limited the commercial application of such active systems.

Accordingly, it is a general object of the present invention to provide an improved transdermal drug delivery system and method.

It is another object of the invention to eliminate or greatly reduce the pain of drug delivery by present skin-penetrating devices, such as needles, fluid jets, iontophoresis, etc.

It is another object of the present invention to provide a transdermal delivery system that does not rely on applied electric fields, yet allows drugs that could not previously be administered by passive diffusion to be so administered.

These and other objects of the present invention will become apparent to those skilled in the art from the following detailed description of the invention and the accompanying drawings.

SUMMARY OF THE INVENTION

The present invention comprises a drug delivery system including an apparatus for mechanically disrupting a layer of skin having a known thickness without substantially disrupting underlying dermis layers below the layer of skin in question and a reservoir for continuously applying the drug to the disrupted area of skin. The apparatus includes a cutter having a plurality of microprotrusions having a height chosen with respect to the layer of skin that is to be disrupted and a stop for preventing the apparatus from penetrating the skin beyond a predetermined distance. In the preferred embodiment of the present invention, the microprotrusions include blades that generate cuts in the layer of skin. The cuts are generated by moving the apparatus parallel to the surface of the skin either at the time of application, during the normal movements of the individual wearing the apparatus, or both. In the preferred embodiment of the present invention, the appropriate length of blade is determined for each individual and delivery site on that individual.

BRIEF DESCRIPTION OF THE DRAWINGS

FIGS. 2–5 are cross-sectional views of a silicon substrate at various stages in the fabrication of a bed of microprotrusions according to the present invention.

FIG. 6 is a cross-sectional view of a mold and a bed of microprotrusions constructed thereon.

DETAILED DESCRIPTION OF THE INVENTION

The present invention is based on the observation that the the epidermis layer under the stratum corneum is approximately 100 $\mu$m thick, and like the stratum corneum, has no blood vessels or nerve endings. While the epidermis does have live cells that are fed by diffusion from the dermis below, it can be penetrated without bleeding or pain. Hence, a microcutter or bed of "needles" can penetrate through the stratum corneum to a depth of the top of the epidermal/dermal interface folds without causing discomfort or bleeding. It has been found experimentally that devices that disrupt both the stratum corneum and epidermis increase the permeablity of the skin significantly over that obtained by merely disrupting the stratum corneum. The increase in permeability is sufficient to allow clinically significant doses of compounds that would otherwise not penetrate the skin to be administered.

The present invention is based on mechanically penetrating or disrupting the stratum corneum and epidermis layers, thereby improving the effectiveness of transdermal delivery of drugs incapable of diffusion through the skin with these layers intact. The simplest embodiment of the present invention comprises a bed of microneedles or microcutters that are just long enough to effectively penetrate the stratum corneum and the epidermis. This bed of microprotrusions can be placed on the skin and moved relative to it, either vertically and/or horizontally, in order to generate a large number of tiny micropenetrations and/or microdisruptions in the epidermis and stratum corneum layers. This bed of microprotrusions can be inexpensively manufactured by one of several technologies commonly referred to as micromachining (micro-mechanics, Micro Electro Mechanical Systems, known as MEMS, etc.).

The problems introduced by the stratum corneum have been recognized for some time. However, the need to also penetrate the epidermis has not been previously appreciated. Techniques that remove both the stratum corneum and epidermis layers, as well as some of the underlying layers are known. For example, techniques in which the epidermis and stratum corneum are removed by placing sticky tape in contact with the skin and then ripping off the tape have been used. Unfortunately, such techniques are painful and, in addition, remove a significant amount of underlying dermis layer. The loss of dermis can result in bleeding and the possibility of infection. Such techniques are impractical for clinical practice, and disrupt the skin such that healing takes a week or longer.

Figure 1:
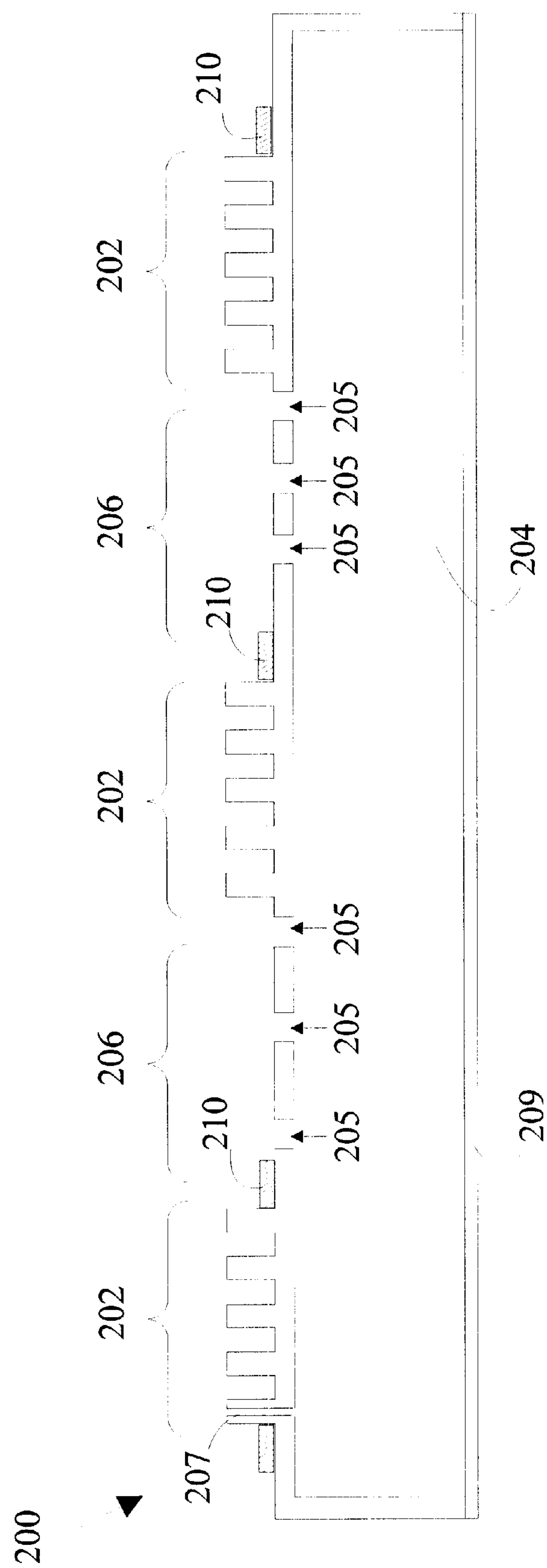
FIG. 1 is a cross-sectional view of a micromechanical patch according to the present invention.

The present invention, however, utilizes a mechanical method for penetrating the stratum corneum and a portion of the epidermis layer without substantially damaging the underlying layers. Hence, blood vessels and nerve endings are not damaged. The simplest embodiment of the present invention is a bed of microprotrusions 202 attached to a drug reservoir 204 as shown in FIG. 1 which is a cross-sectional view of a drug delivery patch 200 according to the present invention. Drug reservoir 204 includes a number of channels 205 through which a drug stored in reservoir 204 can move from reservoir 204 to the skin area adjacent to the disruptions. The areas 206 between the groups of microprotrusions also act as a penetration "stop" that prevents the microprotrusions from penetrating the skin to a depth substantially greater than the height of the microprotrusions. While the drug passages 205 are shown in the stop regions, it will be apparent to those skilled in the art that the passage could be placed in the microprotrusions as shown at 207 to convert the protrusion to a "microneedle".

The manner in which such a bed of microprotrusions can be constructed is illustrated in FIGS. 2–6. Refer first to FIGS. 2–5 which illustrate one of several methods for the fabrication of a bed of microprotrusions in a silicon substrate 13. A layer 12 of silicon dioxide is first deposited on substrate 13. A layer 11 of photoresist is then deposited on oxide 12 and patterned using conventional photolithography techniques. The patterned photoresist layer is used to control the etching of the oxide layer using a fluorine reactive ion etch process which stops on the silicon. The patterned oxide layer is then used as a mask for a chlorine reactive ion etch that penetrates the silicon substrate leaving protrusions 16. The intermediate oxide masks ensure straight sidewalls and consistent edge depths. Alternatively, the microcutter may be composed of the structure shown in FIG. 3 after the top layer of photoresist 11 is removed, provided the silicon oxide layer 12 is deposited with a thickness approximately equal to the thickness of the stratum corneum/epidermis layers.

Yet another alternative method for generating a bed of microprutrusions is illustrated in FIG. 6 which is a cross-sectional view of a mold 24 used to fabricate, for example, a plastic/polymer microcutter 22. Plastic/polymer structures having features of the same general dimensions as those needed for the microcutter have been demonstrated in polystyrene and polyplyimide. However, other plastics/polymers such as polycarbonate may be used. The mold may be constructed as described above. However, it will be apparent to those skilled in the art that a number of different methods for constructing a mold with the necessary microstructure may be utilized.

Once a substrate with the microprotrusions is constructed, the drug channels 205 may be introduced by a conventional pattern etch. Similarly, a depression for the reservoir 204 may be introduced by an etching operation. The drug may be placed in the reservoir by enclosing a pad on which the drug has been absorbed in the depression. The reservoir may then be sealed with a cover 209 over the reservoir.

While the above embodiments have been described in terms of microprotrusions or microneedles, the preferred embodiment for the protrusions is a blade that cuts the skin either when the device is applied or as a result of motion of the device with respect to the skin resulting from the patient's bodily movements during normal activities. Blades have the advantage of being less likely to break during the movement of a microcutter relative to the patient's skin. When the device is applied to the patient's skin, it is pressed against the skin and moved laterally in a direction parallel to the surface of the skin, thereby introducing a number of small shallow microincisions into which the drug from the reservoir will flow. The device is then taped to the patient. Additional movement of the skin relative to the microcutters as the patient moves the area on which the device is attached opens additional microincisions. However, since these microincisions do not extend into a region having blood or nerves, the patient feels no pain.

As noted above, the microcutter must be designed so as to disrupt at least the stratum comeum without interrupting the dermis. The length of the microprotrusions will determine the depth of the cut; however, the precise length needed for any given patient may vary from patient to patient because of differences in the thickness of the stratum corneum between patients and other surface characteristics of the patient's skin.

In general, the patient's skin is not a smooth surface. It contains "hills" and "valleys". In addition, the thickness of the stratum corneum varies from person to person and from place to place on any given person's body. The stratum corneum on the forearm, for example, is typically much thinner than the stratum corneum layer on the heel or the hand. It has been found experimentally, that a microcutter having blades with lengths between 50 $\mu$m and 175 $\mu$m is acceptable for a significant fraction of the population if the device is applied to the forearm. At lengths significantly greater than 175 $\mu$m, the patient feels pain when the device is applied to the forearm and moved laterally across the skin to make the incisions. Blade lengths of less than 50 $\mu$m do not result in microcuts that extend through the stratum comeum and into the epidermis sufficiently to provide the required degree of diffusion for the compound being applied.

One method for dealing with the variation in thickness of these layers is to measure the thickness of these layers for each patient at the intended place of application of the patch. A series of microcutter's having different length blades can be used for this purpose.

If the blade is too short, the stratum comeum will not be penetrated. A dye such as Coomassie Blue can be used to determine when the stratum comeum has been penetrated, since this dye does not stain the stratum comeum but does stain the underlying epidermis layer. Hence, the application of the dye to the microscratch generated by the microcutter will stain the microscratch if the stratum comeum was penetrated. The depth of the stratum comeum can be determined by noting the shortest length microcutter that causes the microscratch to appear stained by the dye. The depth of the epidermis can be determined by observing the length of microcutter which causes the patient to feel pain when the microcutter is moved laterally across the skin. The optimum length of the microcutters is between these two limits. Experimentally, it has been found that painless, bloodless transcutaneous drug delivery is greatly enhanced by micro-disruptions of the interface between the stratum comeum and the epidermis, and particularly, to a depth in the epidermis just above the top of the folds of the epidermis/dermis interface.

It should be noted that the Coomassie Blue dye mentioned above can also be used to determine the minimum length blade needed to disrupt the skin to increase diffusion sufficiently to administer a compound transdermally. It has been observed experimentally that Coomassie Blue will cause a stinging sensation when the microcut penetrates a substantial distance into the epidermis. This stinging sensation results from the dye diffusing into the dermis where it interacts with the nerve endings that are in the dermis. Hence, the optimal length of the microcutter blades can be determined by using a series of microcutter blade lengths and observing whether or not the patient feels a stinging sensation within a few seconds of the application of the dye. A blade length which is less than that which causes pain without the dye, but greater than that which causes pain with the application of the dye has been found to be optimal for the purposes of facilitating the delivery of compounds through the skin.

Figure 7:
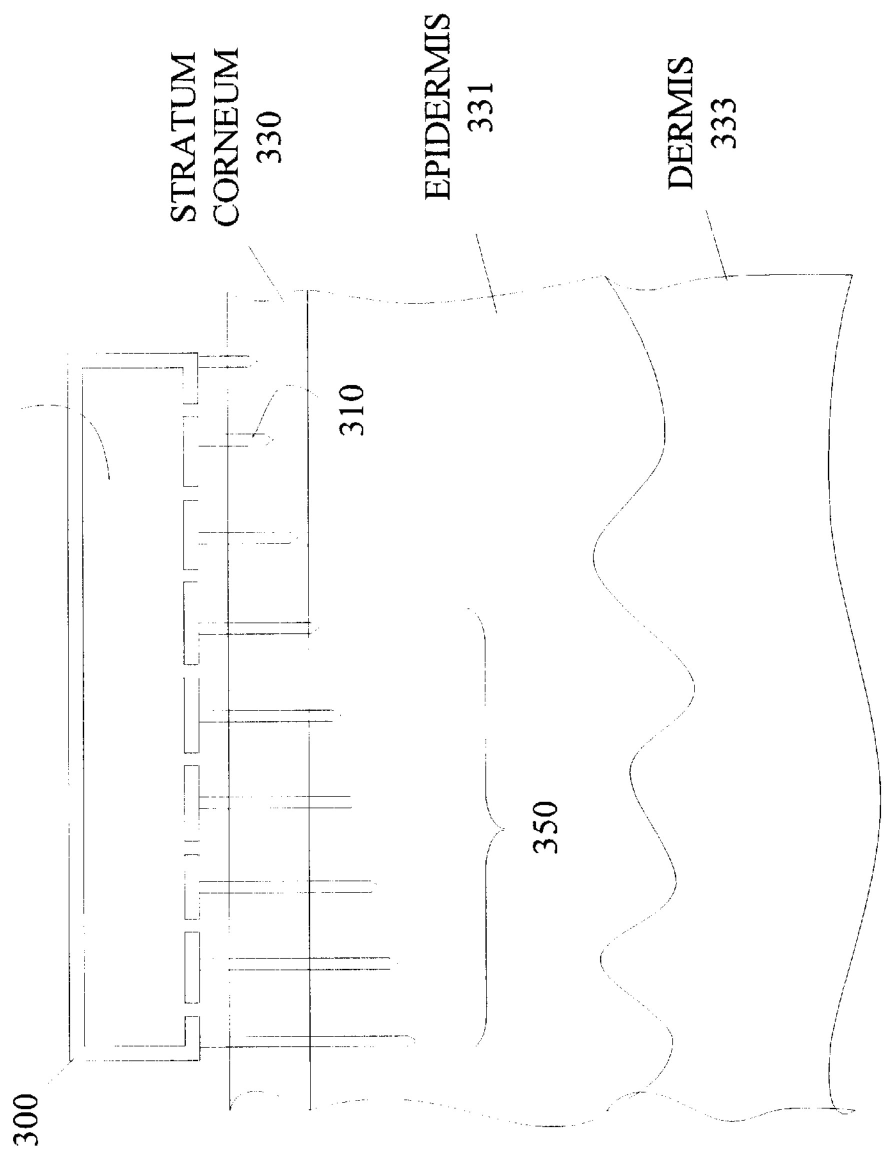
FIG. 7 is a measurement patch.

The measurement of the optimal microcutter length may be facilitated by a patch according to the present invention in which the microprotrusions are of different lengths. Refer now to FIG. 7 which is a cross-section of a specialized patch 300 for use in determining the thickness of the stratum corneum. Patch 300 includes a chamber 302 and a plurality of microcutters of which microcutter 310 is typical. The microcutters can be arranged in rows in which each row consists of microprotrusions of a particular length. The rows are arranged so that the length of the microprotrusions increases from one side of the patch to the other. The range of lengths is chosen such that the minimum length is unlikely to disrupt the stratum corneum 330; while the maximum length is unlikely to disrupt the epidermis 331 and penetrate into the dermis 333. These lengths are chosen with respect to a statistical sampling skin layer thicknesses at a predetermined location on the body for a large segment of the population.

Chamber 302 is filed with Coomassie Blue dye or a similar dye that stains the epidermis, but not the stratum corneum. When the patch is drawn over the patient's skin, a series of microscratches is generated and the dye is applied to the scratches. The excess dye is then wiped off the skin. If the stratum corneum thickness lies within the range of the microcutter lengths on the patch, a series of scratches in which part of the scratches are stained will be generated. The stained scratches will all be on the side of the patch having the longer length microcutters. In the example shown in FIG. 7, the microcutters shown at 350 will all generate scratches that will be stained by the dye. By counting the number of stained scratches and comparing it to a calibration printed on the patch, the depth of stratum corneum can be readily determined.

As noted above, the optimal length of microcutter is that which disrupts the boundary between the stratum corneum and the epidermis without penetrating the epidermis/dermis boundary. Ideally, this depth should be determinable without subjecting the patient to pain. Hence, in the preferred embodiment of the present invention, a plurality of dye patches are used to determine the optimal depth. Each patch has a different range of microcutter lengths. The first patch has the smallest microcutters. If this patch does not provide a series of blue lines when drawn across the skin, the next patch in the series is utilized, and so on. In this manner, the depth of the stratum comeum/epidermis boundary can be determined without cutting into the dermis.

To assure sterility and prevent cross-contamination between patients, the depth determining patches described above are preferably used only once and then discarded. The low cost of construction of a microcutter according to the present invention allows for such disposable use.

While the above described measurement patch utilized a dye that stained only the edidermis, it will be apparent to those skilled in the art that any dye that differentially stains the two layers of skin may be utilized.

While the above-described fabrication techniques utilized silicon substrates to form the microprotrusions directly or through molding of plastics/polymers, metals or the like, it will be apparent to those skilled in the art from the above discussion that microprotrusions may be fabricated as an inexpensive and identical array of microneedles by any one of several technologies known as micromachining, micromechanics, MEMS, or microfabrication techniques. These microelectronic-like technologies typically first employ the deposition onto a substrate of various films on the size scale of the stratum corneum thickness. Examples of typical films include silicon nitride, silicon oxide, polyimide, aluminum, gold, etc. Secondly, a photolithography technique imparts an image of an array of hundreds or thousands of tiny structures to the top film layer. After selective etching, this results in the fabrication of millions of identical microstructures on the size scale of the stratum corneum thickness. Other process steps include wet etching, plasma etching, or reactive ion etching a photosensitive polymer film (resist) on a silicon substrate or wafer as is common in the microelectronics industry. The films may be deposited by chemical vapor deposition techniques prior to the etching operation. The substrate is then bulk and/or surfaced micromachined to achieve the required height.

Various modifications to the present invention will become apparent to those skilled in the art from the foregoing description and accompanying drawings. Accordingly, the present invention is to be limited solely by the scope of the following claims.

What is claimed is:

1. A method for transdermal delivery of a compound to an animal at a site on said animal's skin, said skin comprising a stratum corneum layer, an epidermis layer under said stratum corneum, and a dermis layer under said epidermis, said method comprising the steps of:

determining a depth of a cut that will extend through the stratum corneum of that animal at said delivery site but not penetrate the dermis of that animal at said delivery site; and applying an apparatus at said delivery site to generate a cut extending through said stratum corneum layer, said cut extending into said epidermis but not into said dermis layer, said apparatus comprising:

a plurality of microprotrusions for disrupting the skin at said delivery site, said mircoprotrusions having a length determined by said determined depth;

stop means for preventing said apparatus from penetrating said layer of skin beyond a predetermined distance; and a reservoir having a channel communicating with said layer of skin or one of said underlying dermis layers.

2. The method of claim 1, wherein at least one of said microprotrusions is a blade having an elongated cross-section, said blade being positioned so as to cut said layer of skin when said apparatus is moved relative to said layer of skin.

3. The method of claim 1 wherein said microprotrusions comprise molded polymer or metal microprotrusions.

4. The method of claim 1 wherein said channel comprises a passage through one of said microprotrusions.

5. The method of claim 1 wherein said step of determining a depth comprises the steps of:

moving an apparatus having a microprotrusion of a fixed length and a stop means for preventing said microprotrusion from penetrating the animal to a depth greater than said fixed length, said moving of said apparatus inducing a microcut in said skin; and determining if said microcut extends into the epidermis of that individual at said delivery site.

6. The method of claim 5 wherein said step of determining if said microcut extends into the epidermis of said animal comprising applying a compound to said microcut; and determining if said compound has entered the epidermis of that animal.

7. The method of claim 6 wherein said compound comprises a dye.

8. The method of claim 7 wherein said dye is Coomassie Blue.

* * * * *